United States Patent
Briskin et al.

(10) Patent No.: US 6,514,497 B1
(45) Date of Patent: Feb. 4, 2003

(54) INHIBITION OF LERK-2-MEDIATED CELL ADHESION

(75) Inventors: Michael J. Briskin, Lexington; Lily Zou, Cambridge, both of MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/164,621

(22) Filed: Oct. 1, 1998

Related U.S. Application Data

(60) Provisional application No. 60/060,757, filed on Oct. 2, 1997.

(51) Int. Cl.$^7$ .................. A61K 39/395; C07K 16/28

(52) U.S. Cl. .................. 424/143.1; 424/130.1; 424/137.1; 424/141.1; 424/152.1; 424/172.1; 530/387.1; 530/387.5; 530/388.1; 530/388.22

(58) Field of Search .................. 424/130.1, 134.1, 424/143.1, 152.1, 137.1, 139.1, 141.1, 172.1, 184.1, 185.1, 192.1; 530/387.1, 387.3, 387.9, 388.1, 388.2, 388.22, 388.85, 350, 395

(56) References Cited

U.S. PATENT DOCUMENTS

| | | |
|---|---|---|
| 5,627,267 A | 5/1997 | Lyman et al. |
| 5,728,813 A | 3/1998 | Lyman et al. |

FOREIGN PATENT DOCUMENTS

| | | |
|---|---|---|
| WO | WO 94/11384 | 5/1994 |
| WO | WO 96/02645 | 2/1996 |
| WO | WO 96/26958 | 9/1996 |
| WO | WO97/04091 | 2/1997 |
| WO | WO 97/14966 | 4/1997 |
| WO | WO 99/08696 | 2/1999 |

OTHER PUBLICATIONS

Huang Pharmacol. Therapeutics 2000 86:201–215.*
Holzman, Lawrence, B., et al., "A Novel Immediate–Early Response Gene of Endothelium Is Induced by Cytokines and Encodes a Secreted Protein", *Mol. Cell. Biol.*, 10(11):5830–5838 (1990).
Lai, Cary and Lemke, Greg, "An Extended Family of Protein–Tyrosine Kinase Genes Differentially Expressed in the Vertebrate Nervous System", *Neuron*, 6:691–704 (1991).
Pandey, A., et al., "Receptor Orphans Find a Family", *Current Biology*, 5(9):986–989 (1995).
Pandey, Akhilesh, et al., "Role of B61, the Ligand for the Eck Receptor Tyrosine Kinase, in TNF–α–Induced Angiogenesis", *Science*, 268:567–569 (1995).
Pasquale, Elena B., "Identification of Chicken Embryo Kinase 5, A Developmentally Regulated Receptor–Type Tyrosine Kinase of the Eph Family", *Cell Regulation*, 2:523–534 (1991).

Brambilla, R., et al., "Similarities and Differences in the Way Transmembrane–Type Ligands Interact with the Elk Subclass of Eph Receptors", *Mol. Cell Nuerosci.*, 8(2–3):199–209 (1996).
Brambilla, R., et al., "Membrane–Bound LERK2 Ligand Can Signal Through Three Different Eph–Related Receptor Tyrosine Kinases", *EMBO J.*, 14(13):3116–3126 (1995).
Wang, Hai U., et al., "Molecular Distinction and Angiogenic Interaction between Embryonic Arteries and Veins Revealed by ephrin–B2 and Its Receptor Eph–B4", *Cell*, 93:741–753 (1998).
Labrador, J.P., et al., "The N–Terminal Globular Domain of Eph Receptors is Sufficient for Ligand Binding and Receptor Signaling", *EMBO J*, 16(13):3889–3897 (1997).
Tanaka, M., et al., "Interaction of EphB2–Tyrosine Kinase Receptor and its Ligand Conveys Dorsalization Signal in *Xenopus Laevis* Development", *Oncogene*, 17(12):1509–1516 (1998).
Abrahamson, D.R., et al., "Origins and Formation of Microvasculature in the Developing Kidney", *Kidney International*, 54(67):S7–S11 (1998).
Bruckner, K. and Klein, R., "Signaling by Eph Receptors and Their Ephrin Ligands", *Curr. Opin. Neurobiol.*, 8(3):375–382 (1998).
Stein, E., et al., "Eph Receptors Discriminate Specific Ligand Oligomers to Determine Alternative Signaling Complexes, Attachment, and Assembly Responses", *Genes Dev.*, 12(5):667–678 (1998).
Flanagan, J.G. and Vanderhaeghen, P., "The Ephrins and Eph Receptors in Neural Development", *Annu. Rev. Neurosci.*, 21:309–345 (1998).
Bergemann, A.D., et al., "Ephrin–B3, a Ligand for the Receptor EphB3, Expressed at the Midline of the Developing Neural Tube", *Oncogene*, 16(4):471–480 (1998).
Stein, E., et al., "Nck Recruitment to Eph Receptor, EphB1/ELK, Couples Ligand Activation to c–Jun Kinase", *J. Biol. Chem.*, 273(3):1303–1308 (1998).
Jones, T.L., et al., "Loss of Cell Adhesion in *Xenopus Laevis* Embryos Mediated by the Cytoplasmic Domain of XLerk, an Erythopoietin–Producing Hepatocellular Ligand", *Proc. Natl. Acad. Sci. USA*, 95(2):576–581 (1998).
Lemke, G., "A Coherent Nomenclature of Eph Receptors and Their Ligands", *Mol. Cell. Neurosci.*, 9(5–6):331–332 (1997).

(List continued on next page.)

Primary Examiner—Phillip Gambel
Assistant Examiner—Jessica H. Roack
(74) *Attorney, Agent, or Firm*—Hamilton, Brook, Smith & Reynolds, PC

(57) ABSTRACT

Methods of modulating LERK-2-mediated cell adhesion, as well as methods of modulating angiogenesis and inflammation are described. Also described are agents such as antibodies which can modulate LERK-2-mediated cell adhesion, as well as methods of treating angiogenic diseases and inflammatory diseases.

8 Claims, 8 Drawing Sheets-

OTHER PUBLICATIONS

Braisted, J.E., et al., "Graded and Lamina–Specific Distributions of Ligands of EphB Receptor Tyrosine Kinases in the Developing Retinotectal System", *Dev. Biol.,* 191(1):14–28 (1997).

Orioli, D. and Klein R., "The Eph Receptor Family: Axonal Guidance by Contact Repulsion", *Trends Genet.,* 13(9):354–359 (1997).

Krull, C.E., et al., "Interactions of Eph–Related Receptors and Ligands Confer Rostrocaudal Pattern to Trunk Neural Crest Migration", *Curr. Biol.,* 7(8):571–580 (1997).

Holland, S.J., et al., "Juxtamembrane Tyrosine Residues Couple the Eph Family Receptor EphB2/Nuk to Specific SH2 Domain Proteins in Neuronal Cells", *EMBO J,* 16(13):3877–3888 (1997).

Lackmann, M., et al., "Ligand for EPH–Related Kinase (LERK) 7 is the Preferred High Affinity Ligand for the HEK Receptor", *J. Biol. Chem.* 272(26):16521–16530 (1997).

Jones, T.L., et al., "Identification of XLerk, an Eph Family Ligand Regulated During Mesoderm Induction and Neurogenesis in *Xenopus Laevis*", *Oncogene,* 14(18):2159–2166 (1997).

Stein, Elke, et al., "Eph Family Receptors and Ligands in Vascular Cell Targeting and Assembly", *Trends in Cardiovascular Medicine,* 7(8):329–334 (1997).

Meima, Leonie, et al., "Lerk2 (Ephrin–B1) Is a Collapsing Factor for a Subset of Cortical Growth Cones and Acts by a Mechanism Different from AL–1 (Ephrin–A5)", *Molecular and Cellular Neuroscience,* 9(4):314–328 (1997).

Beckman, M. Patricia, et al., "Molecular Characterization of a Family of Ligands for Eph–Related Tyrosine Kinase Receptors", *The EMBO Journal,* 13(16):3757–3762 (1994).

Böhme, Beatrix, et al., "Cell–Cell Adhesion Mediated by Binding of Membrane–anchored Ligand LERK–2 to the EPH–Related Receptor Human Embroyonal Kinase 2 Promotes Tyrosine Kinase Activity", *The Journal of Biological Chemistry,* 271(40):24747–24752 (1996).

Daniel, Thomas O., et al., "ELK and LERK–2 in Developing Kidney and Microvascular Endothelial Assembly", *Kidney International,* 50(57):S73–S81 (1996).

* cited by examiner

Immunostaining with 4A1 and anti-CD4

Immunostaining with 4A1 and anti-CD45RO

Gate on lymphocytes      Gate on monocytes

IgG1      IgG1

4A1      4A1

SEQUENCE LISTING

<160> NUMBER OF SEQ ID NOS: 4

<210> SEQ ID NO 1
<211> LENGTH: 17
<212> TYPE: DNA
<213> ORGANISM: Artificial Sequence
<220> FEATURE:
<223> OTHER INFORMATION: Primer Sequence

<400> SEQUENCE: 1
gcccccgagc agaagca                                                    17

<210> SEQ ID NO 2

-continued

```
<211> LENGTH: 21
<212> TYPE: DNA
<213> ORGANISM: Artificial Sequence
<220> FEATURE:
<223> OTHER INFORMATION: Primer Sequence

<400> SEQUENCE: 2
caggaagatg atgatgagca g                                              21

<210> SEQ ID NO 3
<211> LENGTH: 30
<212> TYPE: DNA
<213> ORGANISM: Artificial Sequence
<220> FEATURE:
<223> OTHER INFORMATION: Primer Sequence

<400> SEQUENCE: 3
ggagcttcca ccatggctcg gcctgggcag                                     30

<210> SEQ ID NO 4
<211> LENGTH: 29
<212> TYPE: DNA
<213> ORGANISM: Artificial Sequence
<220> FEATURE:
<223> OTHER INFORMATION: Primer Sequence

<400> SEQUENCE: 4
ggactagtgc cacctttgag ttgaagaag                                      29
```

INHIBITION OF LERK-2-MEDIATED CELL ADHESION

RELATED APPLICATIONS

This application claims the benefit of U.S. Provisional Application No. 60/060,757, filed Oct. 2, 1997, the entire teachings of which are incorporated herein by reference.

BACKGROUND OF THE INVENTION

In order to coordinate the activities necessary for survival of a multicellular organism, the individual cells of the organism must communicate with each other via cell-surface receptors and their ligands. The known receptors are generally classified based on the particular method of signal transduction (translation of an extracellular signal into an intracellular signal) which is most characteristic of the receptor class. One class of receptors is the group of receptor protein-tyrosine kinases, which have intracellular kinase domains that are activated by binding of one or more ligands, resulting in autophosphorylation of specific tyrosine residues and activation of intracellular signalling molecules.

The largest subfamily of the receptor protein-tyrosine kinases (RPTK) is the Eph subfamily, characterized by the oncogene eph (Hirai et al., *Science* 238:1717–1720 (1987)). The ligands for the Eph RPTKs constitute a rapidly expanding group of molecules which are either transmembrane or glycosylphosphatidylinositol (GPI)-linked (Pandey et al., *Current Biology* 5(9) :986–989 (1995)). It is likely that the Eph receptor-ligand interactions play important roles in the growth, development and survival of multicellular organisms.

SUMMARY OF THE INVENTION

The invention pertains to a method of modulating LERK-2-mediated cell adhesion, comprising the step of contacting a cell expressing LERK-2 and/or a cell expressing a receptor for LERK-2 with an inhibitor or promoter of LERK-2-mediated cell adhesion. In a particular embodiment, the receptor for LERK-2 is selected from the group consisting of Nuk, Cek5, Tyro5 and ERK, and in a preferred embodiment the receptor for LERK-2 is Nuk. In one embodiment, the cell expressing a receptor for LERK-2 is a lymphoid cell, particularly a T cell.

In one embodiment of the method, the inhibitor is selected from the group consisting of an antibody or functional antibody fragment which inhibits LERK-2-mediated cell adhesion (e.g., an anti-LERK-2 antibody), soluble LERK-2 and a LERK-2-Ig chimera. In a particular embodiment, the anti-LERK-2 antibody or fragment is selected from the group consisting of monoclonal antibody 2A1, a functional antibody fragment of 2A1, monoclonal antibody 4A1 and a functional antibody fragment of 4A1.

The invention also relates to a method of detecting or identifying an inhibitor or promoter of LERK-2-mediated cell adhesion, comprising the steps of combining an agent to be tested with a composition comprising a cell expressing LERK-2 and a composition comprising a cell expressing a receptor for LERK-2 under conditions suitable for binding of LERK-2 to a receptor for LERK-2, and detecting or measuring cell adhesion between the cell expressing LERK-2 and the cell expressing a receptor for LERK-2, whereby inhibition or promotion of cell adhesion by the agent is indicative that the agent is an inhibitor or promoter, respectively. The invention also pertains to inhibitors and promoters (i.e., modulators) identified by the described methods.

For example, modulators which can be identified as described herein include modulating antibodies, e.g., antibodies which inhibit or promote LERK-2-mediated cell adhesion. Modulating antibodies can be an antibody or functional antibody fragment which modulates LERK-2-mediated cell adhesion, such as an antibody or fragment which modulates binding of LERK-2 to a receptor for LERK-2. In a particular embodiment, the antibody or functional antibody fragment is an anti-LERK-2 antibody.

In one embodiment the invention relates to an antibody or functional antibody fragment which inhibits LERK-2-mediated cell adhesion, such as an antibody or fragment which inhibits binding of LERK-2 to a receptor for LERK-2. In a particular embodiment, the antibody or functional antibody fragment is an anti-LERK-2 antibody. In a preferred embodiment, the antibody or functional antibody fragment is selected from the group consisting of monoclonal antibody 2A1, monoclonal antibody 4A1, a functional antibody fragment of 2A1 and a functional antibody fragment of 4A1. The invention also relates to an antibody or functional antibody fragment which can compete with monoclonal antibody 2A1 or monoclonal antibody 4A1 for binding to LERK-2 or portion thereof.

The invention also pertains to the hybridoma cell line deposited under ATCC Accession No. HB-12412 and to the hybridoma cell line deposited under ATCC Accession No. HB-12413. The invention further relates to a monoclonal antibody or antigen binding fragment thereof produced by the hybridoma cell line deposited under ATCC Accession No. HB-12412 or HB-12413.

The invention also relates to a method for treating an angiogenic disease, comprising administering to a mammal a therapeutically effective amount of an inhibitor of LERK-2-mediated cell adhesion, whereby angiogenesis is reduced.

The invention further pertains to a method for treating an inflammatory disease or condition, comprising administering to a mammal a therapeutically effective amount of an inhibitor of LERK-2-mediated cell adhesion, whereby inflammation is reduced.

The invention pertains to a method of antitumor therapy, comprising administering to a mammal a therapeutically effective amount of an inhibitor of LERK-2-mediated cell adhesion, whereby angiogenesis is reduced, thereby inhibiting tumor growth.

The invention also relates to a method for enhancing angiogenesis, comprising administering to a mammal a therapeutically effective amount of a promoter of LERK-2-mediated cell adhesion, whereby angiogenesis is enhanced.

BRIEF DESCRIPTION OF THE DRAWINGS

FIG. 1A shows staining of CD4 positive mononuclear cells, the first column gating on all lymphocytes and the second gating on monocytes; both lymphocytes and monocytes express CD4). Both monocytes and lymphocytes show positive results with anti-LERK-2 antibody 4A1. FIG. 1B shows staining using CD14, a monocyte-specific marker, and 4A1. In the first column all cells are largely confined to the lower axis while in the second column cells are in the upper right column indicating they are positive for both LERK-2 and CD14 (LERK-2 positive monocytes). FIG. 1C shows that LERK-2 reactivity is associated with the memory marker CD45RO. For lymphocytes, the lower right quadrant shows similar levels of reactivity, indicating that CD45RO negative populations (naive cells) non-specifically bind antibody. Cells are seen only in the upper right quadrant for the LERK-2 monoclonal antibody and not the control, indicating that a memory subset of lymphocytes is positive for LERK-2.

In FIG. 2A, LERK-2 expression is also seen in unstimulated HUVEC cultures while expression is slightly increased by 24-hour incubation with TNF-α. The bole tracing represents a control monoclonal antibody (IgG1), while the open tracing is reactivity with anti-LERK-2 monoclonal antibody 4A1.

DETAILED DESCRIPTION OF THE INVENTION

Figure 1A:
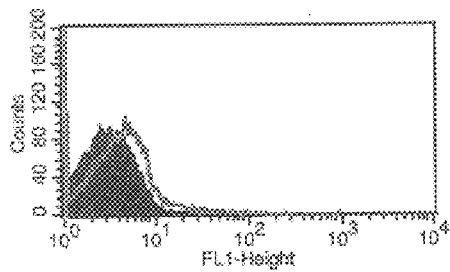
FIGS. 1A–1C show the results of FACS analysis of the expression of LERK-2 (as assessed by binding of anti-LERK-2 antibody 4A1) on leukocytes.
Figure 1A:
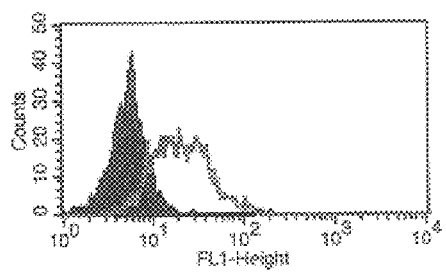

LERK-2 (Ligand for eph-related kinase-2; Beckmann et al., *EMBO J.* 13(16):3757–3762 (1994)) has been identified as a ligand for the elk and hek tyrosine kinase receptors, which are members of the Eph RPTK family. LERK-2 is a transmembrane protein which is related by sequence homology to LERK-1 (also known as B61; Beckmann et al., *EMBO J.* 13(16):3757–3762 (1994)).

Eph RPTKs are characterized as encoding a structurally-related cysteine rich extracellular domain containing a single immunoglobin-like loop near the N-terminus and two fibronectin III repeats adjacent to the plasma membrane. The structure of the extracellular region is thought to determine ligand binding specificity. Examples of Eph RPTK family members include mouse Nuk (GenBank Accession No. L25890) and its homologs Hek5 and Cek5 in chickens (Pasquale, *Cell Regulation* 2:523–534 (1991)), Sek3 in mice, Tyro5 in rats (Lai and Lemke, Neuron 6:691–704 (1991)) and Erk in humans. Expression of Nuk was found to be essential for formation of at least one commissure in the brain, the medial tract of the anterior commissure, as well as for other brain structures (WO 97/14966 (Pawson et al.)).

As described herein below, an expression cloning system was used to isolate a cDNA from a human mesenteric lymph node library which, upon transfection into CHO/P cells, mediates binding of the murine T cell lymphoma, TK1, through the Nuk receptor. Sequencing of the isolated cDNA revealed it to be LERK-2. The interaction of lymphoid cells with LERK-2 represents a step in cell adhesion cascades that has not previously been described.

As described herein, it has been discovered that LERK-2 can mediate cell-cell adhesion between cells expressing LERK-2 and cells expressing a receptor for LERK-2, e.g., cells expressing an Eph RPTK such as Nuk or its homologs. It has further been discovered that Nuk, an RPTK which binds LERK-2, is present on T cell subsets, e.g., TK-1 cell lines, and that LERK-2/Nuk interactions mediate adhesion between cells expressing the ligand and cells expressing the receptor. It has also been discovered that agents which alter the LERK-2/receptor interaction can modulate this cell adhesion, thereby modulating the signals propagated by the stimulation of the receptor through binding of LERK-2. Accordingly, the cellular processes which are regulated by the signals transduced by the LERK-2/RPTK interaction, such as angiogenesis, inflammation and leukocyte trafficking, can be modulated as described herein by modulating LERK-2-mediated cell adhesion.

Angiogenesis, the generation of capillaries, is virtually absent in healthy adult organisms and is restricted to a few instances, including wound healing and the formation of the corpus luteum, endometrium and placenta. Endothelial cells play a key role in the formation of new capillaries, and the neovascularization process occurs via a series of sequential steps, which are similar regardless of the nature of the inducing stimulus. Under normal physiological conditions in the healthy adult mammal, except during cyclical changes in the female reproductive tract or in response to wound healing, the coordinated sequential cellular events leading to new capillaries are spatially and temporally restricted so that inhibitory influences on neovascularization predominate.

However, in certain pathological conditions angiogenesis is dramatically enhanced and is no longer self-limited (Maugh, *Science* 212:1374–1375 (1981); Auerback, *Lymphokines* 4:69 (1981)). Angiogenesis is a major component of some opthalmological pathologies such as corneal graft rejection, corneal neovascularization following injury or infection, diabetic retinopathy, retrolental fibroplasia and neovascular glaucoma (Garner, *Int. Rev. Exp. Pathol.* 284:249–307 (1986)). It is also a significant factor in many ulcerative diseases such as rheumatoid arthritis, ulcerative colitis and gastric ulcer. In addition, angiogenesis is a major component in pathological but nonmalignant conditions such as hemangioma, angiofibroma of the nasopharynx, avascular necrosis of bone, and psoriasis.

Perhaps the clinically most important manifestation of pathological angiogenesis is that induced by solid tumors (Folkman, *Adv. Cancer Res.* 43:175–203 (1985); Folkman, *Nature Medicine* 1(1) (1995)). In order for a neoplasm to grow progressively as a solid mass consisting of layers of living cells more than a few millimeters thick, it must induce nearby capillaries to sprout and develop a new vascular network around and within the tumor. The new vascular network supplies the tumor with vital nutrients and oxygen and provides a removal route for toxic products of active cell metabolism. Furthermore, new tumor vessels provide an exit for tumor cells to metastize to distant sites. Thus, the progressive growth of a solid tumor to develop into a life-threatening malignancy is strictly dependent on angiogenesis.

Members of the LERK ligand family have been shown to be involved in the angiogenic process. For example, LERK-1 has been shown in vitro to be angiogenic for human umbilical vein endothelial cells (HUVECs) via the Eck receptor, and has been shown to promote corneal neovascularization in a rat model (Pandey et al., *Science* 268:567–569 (1995)). LERK-2 has been shown to be angiogenic for a human renal microvascular endothelial cell line via the Elk receptor (HRMEC; Daniel et al., *Kidney International* 50(Suppl. 57):S-73-S-81 (1996)).

LERK-1 has also been shown to be an immediate early response gene in endothelial cells; its expression is induced by proinflammatory factors such as tumor necrosis factor-α (TNF-α), interleukin-1 and lipopolysaccharide (Holzman et al., *Mol. Cell. Biol.* 10:5830–5838 (1990)). LERK-2 has similarly been shown to be induced by TNF-α in endothelial cells (Beckmann et al., *EMBO J.* 13:3757–3762 (1994)).

Inflammatory disorders or conditions generally share several features which are agreed to be characteristic of the inflammation process. These include fenestration of the microvasculature, leakage of blood elements into the interstitial spaces, and migration of leukocytes into the inflamed tissue. On a macroscopic level, this is usually accompanied by the familiar clinical signs of erythema, edema, tenderness (hyperalgesia), and pain. Inflammatory diseases such as chronic inflammatory pathologies and vascular inflammatory pathologies include, for example, aneurysms, hemorrhoids, sarcoidosis, chronic inflammatory bowel disease, delayed type hypersensitivity reaction, allograft rejection, ulcerative colitis, Crohn's disease, disseminated intravascular coagulation, atherosclerosis, and Kawasaki's pathology. Inflammatory diseases also include coronary artery disease, hypertension, stroke, asthma, psoriasis, nephritis, chronic hepatitis, multiple sclerosis, peripheral neuropathy, chronic or recurrent sore throat, laryngitis, tracheobronchitis, chronic vascular headaches (including migraines, cluster headaches and tension headaches), pneumonia and bacterial or viral infection.

The present invention relates to a method of modulating (i.e., inhibiting or promoting) LERK-2-mediated cell adhesion. In a preferred embodiment, the invention pertains to a method of modulating LERK-2/Nuk-mediated cell adhesion (i.e., cell adhesion mediated by the interaction or binding of LERK-2 and Nuk). As used herein, "LERK-2-mediated cell adhesion" means cell adhesion mediated by binding of LERK-2 to its corresponding Eph RPTK (i.e., a LERK-2 receptor or receptor for LERK-2), thereby mediating adhesion between the cell which expresses LERK-2 and the cell which expresses the Eph RPTK. Eph RPTKs which bind to LERK-2 include, but are not limited to, Cek1O, Sek-4, Tyro6, HEK2, Cek5, Nuk (Sek-3), Tyro5, ERK, Cek6 and Elk.

The method of the invention comprises contacting at least one cell selected from the group consisting of a cell expressing LERK-2 and a cell expressing a receptor for LERK-2 with an inhibitor or promoter of LERK-2-mediated cell adhesion. Suitable cells can be cells which normally (in nature) express LERK-2 or a receptor for LERK-2, or can be cells which have been engineered, e.g., by recombinant technology, to express LERK-2 or a receptor for LERK-2. In vivo expression can be accomplished via somatic cell expression according to suitable methods (see, e.g. U.S. Pat. No. 5,399,346). In this embodiment, nucleic acid encoding the protein can be incorporated into a retroviral, adenoviral or other suitable vector (preferably, a replication deficient infectious vector) for delivery, or can be introduced into a transfected or transformed host cell capable of expressing the protein for delivery.

In particular embodiments, the cells expressing LERK-2 or receptor for LERK-2 are lymphoid cells (e.g., leukocytes, including lymphocytes such as T cells) or endothelial cells.

In a preferred embodiment, the receptor for LERK-2 is selected from the group consisting of Nuk, Cek5, Tyro5 and ERK. In a particularly preferred embodiment the LERK-2 receptor is Nuk.

Suitable inhibitors for use in the invention include, but are not limited to, anti-LERK-2 antibodies or functional antibody fragments thereof, anti-Eph RPTK antibodies or functional antibody fragments thereof, e.g., anti-Nuk antibodies, soluble LERK-2 and LERK-2-Ig chimeras. Suitable promoters include isolated LERK-2 or LERK-2 chimeras, as well as LERK-2 mimics. As used herein, a "LERK-2 mimic" is an agent which can activate, e.g., by binding, a LERK-2 receptor, e.g., an Eph RPTK such as Nuk, to induce the same or similar downstream signaling events as those induced by LERK-2. LERK-2 mimics can include, for example, peptides, small molecules and antibodies which can activate a LERK-2 receptor.

For instance, polyclonal and monoclonal antibodies which bind to LERK-2 or a receptor for LERK-2 are within the scope of the invention. A mammal, such as a mouse, hamster or rabbit, can be immunized with an immunogenic form of LERK-2 or LERK-2 receptor (i.e., an antigenic fragment of LERK-2 or LERK-2 receptor which is capable of eliciting an antibody response) such as isolated and/or recombinant peptide (including synthetic molecules, such as synthetic peptides). Preparation of immunizing antigen (e.g., a peptide conjugated to a suitable carrier, such as keyhole limpet hemocyanin, serum albumin, etc.), and polyclonal and monoclonal antibody production can be performed using any suitable technique. Techniques for conferring immunogenicity on a protein or peptide include conjugation to carriers or other techniques well known in the art. The protein or polypeptide can be administered in the presence of an adjuvant. The progress of immunization can be monitored by detection of antibody titers in plasma or serum. Standard ELISA or other immunoassays can be used with the immunogen as antigen to assess the levels of antibody.

Following immunization, anti-peptide antisera can be obtained, and if desired, polyclonal antibodies can be isolated from the serum. Monoclonal antibodies can also be produced by standard techniques which are well known in the are (see e.g., Kohler et al., *Nature*, 256: 495–497 (1975) and *Eur. J. Immunol.* 6: 511–519 (1976); Milstein et al., *Nature* 266: 550–552 (1977); Koprowski et al., U.S. Pat. No. 4,172,124; Harlow, E. and D. Lane, 1988, *Antibodies: A Laboratory Manual*, (Cold Spring Harbor Laboratory: Cold Spring Harbor, N.Y.); *Current Protocols In Molecular Biology*, Vol. 2 (Supplement 27, Summer '94), Ausubel, F.M. et al., Eds., (John Wiley & Sons: New York, N.Y.), Chapter 11, (1991)).

One standard approach to the production of monoclonal antibodies is that described by Kohler et al., (1975). In this method a subject animal (e.g., mouse, rat or other rodent) is immunized with the material against which the antibodies are desired (e.g., LERK-2 or portion thereof or LERK-2 receptor or portion thereof). The animal's immune system generates antibodies against the material via its B cells, which are localized in the animal's spleen. The spleen (or lymph) is removed and treated to isolate individual cells. These cells are fused with cell lines which are immortal in culture (e.g., a myeloma cell line such as SP2/0) in the presence of an agent which facilitates cell fusion (e.g., polyethylene glycol). The fused cells yield hybridomas, each of which produces antibodies of a particular epitopic specificity. Suitable screening procedures are then carried out to identify and isolate hybridomas producing antibodies with the desired epitopic specificity (monoclonal antibodies). For example, cells which produce antibodies with the desired specificity can be selected by a suitable assay (e.g., ELISA).

In order to identify the particular epitopic specificity of a selected monoclonal antibody, a panel of chimeras comprising selected portions of the antigen in combination with selected portions of another suitable molecule can be constructed by transferring restriction fragments flanked by specific restriction sites (e.g., BamHI, AflII, ClaI, EcoRI, and XbaI sites). The constructs can be transferred into an appropriate vector, under control of an appropriate promoter, and transfected in CHO-k1 cells as described by Perret et al. (*Biochem. Biophys. Res. Commun.* 17:1044 (1990)). Transfectants can be stained with the selected monoclonal antibody to determine the epitopic specificity of the particular antibody.

Murine hybridomas producing monoclonal antibodies 2A1 and 4A1 were deposited under the terms of the Budapest Treaty at the American Type Culture Collection, 10801 University Boulevard, Manassas, Va. 20110, on behalf of LeukoSite, Inc., 215 First Street, Cambridge, Mass. 02142, on Oct. 2, 1997, and were assigned ATCC Accession Nos. HB-12412 and HB-12413, respectively.

In a preferred embodiment of the invention, the inhibitor is selected from the group consisting of monoclonal antibody 2A1 (produced by the murine hybridoma deposited under ATCC Accession No. HB-12412), monoclonal antibody 4A1 (produced by the murine hybridoma deposited under ATCC Accession No. HB-12413), functional antibody fragments of 2A1, functional antibody fragments of 4A1, an antibody or functional antibody fragment thereof which can compete with monoclonal antibody 2A1 or 4A1 for binding to LERK-2 or portion thereof, or an antibody or functional antibody fragment thereof which has the same or similar epitopic specificity as that of 2A1 or 4A1. In a particularly preferred embodiment, the inhibitor (e.g., antibody or functional antibody fragment) selectively inhibits the interaction of LERK-2 with Nuk.

The invention also relates to monoclonal antibody 2A1, monoclonal antibody 4A1, functional antibody fragments of 2A1, functional antibody fragments of 4A1, an antibody or functional antibody fragment thereof which can compete with monoclonal antibody 2A1 or 4A1 for binding to LERK-2 or portion thereof, or an antibody or functional antibody fragment thereof which has the same or similar epitopic specificity as that of 2A1 or 4A1. Also included within the scope of the invention are the hybridoma cell line deposited under ATCC Accession No. HB-12412, the hybridoma cell line deposited under ATCC Accession No. HB-12413, a monoclonal antibody or antigen binding fragment thereof produced by the hybridoma cell line deposited under ATCC Accession No. HB-12412, and a monoclonal antibody or antigen binding fragment thereof produced by the hybridoma cell line deposited under ATCC Accession No. HB-12413. These antibodies have utility as inhibitors of LERK-2-mediated cell adhesion, as well as reagents for immunostaining of cells and tissues to identify expression of LERK-2.

The cell lines of the present invention have uses other than for the production of the monoclonal antibodies. For example, the cell lines of the present invention can be fused with other cells (such as suitably drug-marked human myeloma, mouse myeloma, human-mouse heteromyeloma or human lymphoblastoid cells) to produce additional hybridomas, and thus provide for the transfer of the genes encoding the monoclonal antibodies. In addition, the cell lines can be used as a source of nucleic acids encoding the anti-LERK-2 immunoglobulin chains, which can be isolated and expressed (e.g., upon transfer to other cells using any suitable technique (see e.g., Cabilly et al., U.S. Pat. No. 4,816,567; Winter, U.S. Pat. No. 5,225,539)).

Other suitable methods of producing or isolating antibodies which inhibit LERK-2-mediated cell adhesion can used, including, for example, methods which select recombinant antibody from a library, or which rely upon immunization of transgenic animals (e.g., mice) capable of producing a full repertoire of human antibodies (see e.g., Jakobovits et al., *Proc. Natl. Acad. Sci. USA*, 90: 2551–2555 (1993); Jakobovits et al., *Nature*, 362: 255–258 (1993); Lonberg et al., U.S. Pat. No. 5,545,806; Surani et al., U.S. Pat. No. 5,545,807).

Single chain antibodies, and chimeric, humanized or primatized (CDR-grafted) antibodies, as well as chimeric or CDR-grafted single chain antibodies, comprising portions derived from different species, are also encompassed by the present invention and the term "antibody". The various portions of these antibodies can be joined together chemically by conventional techniques, or can be prepared as a contiguous protein using genetic engineering techniques. For example, nucleic acids encoding a chimeric or humanized chain can be expressed to produce a contiguous protein. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M.S. et al., WO 86/01533; Neuberger, M.S. et al., European Patent No. 0,194,276 B1; Winter, U.S. Pat. No. 5,225,539; and Winter, European Patent No. 0,239,400 B1. See also, Newman, R. et al., *BioTechnology*, 10: 1455–1460 (1992), regarding primatized antibody, and Ladner et al., U.S. Pat. No. 4,946,778 and Bird, R.E. et al., *Science*, 242: 423–426 (1988)) regarding single chain antibodies.

In addition, functional fragments of antibodies, including fragments of chimeric, humanized, primatized or single chain antibodies, can also be produced. Functional fragments of the foregoing antibodies retain at least one modulation function of the full-length antibody from which they are derived. Preferred functional fragments retain an antigen binding function of a corresponding full-length antibody (e.g., specificity for LERK-2 or an Eph receptor for LERK-2). Particularly preferred functional fragments retain the ability to inhibit LERK-2-mediated cell adhesion. For example, in one embodiment, a functional fragment can inhibit the interaction of LERK-2 with a receptor for LERK-2 (e.g., Nuk), thereby inhibiting one or more receptor-mediated functions, such as angiogenesis, inflammation, or leukocyte trafficking.

For example, antibody fragments capable of binding to LERK-2 or portion thereof or to a LERK-2 receptor or portion thereof, including, but not limited to, Fv, Fab, Fab' and F(ab')$_2$ fragments, are encompassed by the invention. Such fragments can be produced by enzymatic cleavage or by recombinant techniques. For instance, papain or pepsin cleavage can generate Fab or F(ab')$_2$ fragments, respectively. Antibodies can also be produced in a variety of truncated forms using antibody genes in which one or more stop codons has been introduced upstream of the natural stop site. For example, a chimeric gene encoding a F(ab')$_2$ heavy chain portion can be designed to include DNA sequences encoding the CH$_1$ domain and hinge region of the heavy chain.

The term "humanized immunoglobulin" as used herein refers to an immunoglobulin comprising portions of immunoglobulins of different origin, wherein at least one portion is of human origin. Accordingly, the present invention relates to a humanized immunoglobulin having binding specificity for LERK-2 or a receptor for LERK-2, said immunoglobulin comprising an antigen binding region of nonhuman origin (e.g., rodent) and at least a portion of an immunoglobulin of human origin (e.g., a human framework region, a human constant region or portion thereof). For example, the humanized antibody can comprise portions derived from an immunoglobulin of nonhuman origin, such as a mouse, and from immunoglobulin sequences of human origin (e.g., a chimeric immunoglobulin), joined together chemically by conventional techniques (e.g., synthetic) or prepared as a contiguous polypeptide using genetic engineering techniques (e.g., DNA encoding the protein portions of the chimeric antibody can be expressed to produce a contiguous polypeptide chain). Another example of a humanized immunoglobulin of the present invention is an immunoglobulin containing one or more immunoglobulin chains comprising a CDR of nonhuman origin (e.g., one or more CDRs derived from an antibody of nonhuman origin) and a framework region derived from a light and/or heavy chain of human origin (e.g., CDR-grafted antibodies with or without framework changes). In one embodiment, the humanized immunoglobulin can compete with 2A1 or 4A1 monoclonal antibody for binding to LERK-2. Chimeric or CDR-grafted single chain antibodies are also encompassed by the term humanized immunoglobulin. See, e.g., Cabilly et al., U.S. Pat. No. 4,816,567; Cabilly et al., European Patent No. 0,125,023 B1; Queen et al., European Patent No. 0,451,216 B1; Boss et al., U.S. Pat. No. 4,816,397; Boss et al., European Patent No. 0,120,694 B1; Neuberger, M.S. et al., WO 86/01533; Neuberger, M.S. et al., European Patent No. 0,194,276 B1; Winter, U.S. Pat. No. 5,225,539; Winter, European Patent No. 0,239,400 B1; Padlan, E.A. et al., European Patent Application No. 0,519,596 A1. See also, Ladner et al., U.S. Pat. No. 4,946,778; Huston, U.S. Pat. No. 5,476,786; and Bird, R.E. et al., Science, 242: 423–426 (1988)), regarding single chain antibodies.

Such humanized immunoglobulins can be produced using synthetic and/or recombinant nucleic acids to prepare genes (e.g., cDNA) encoding the desired humanized chain. For example, nucleic acid (e.g., DNA) sequences coding for humanized variable regions can be constructed using PCR mutagenesis methods to alter DNA sequences encoding a human or humanized chain, such as a DNA template from a previously humanized variable region (see e.g., Kamman, M., et al., Nucl. Acids Res., 17: 5404 (1989)); Sato, K., et al., Cancer Research, 53: 851–856 (1993); Daugherty, B. L. et al., Nucleic Acids Res., 19(9): 2471–2476 (1991); and Lewis, A. P. and J. S. Crowe, Gene, 101: 297–302 (1991)). Using these or other suitable methods, variants can also be readily produced. In one embodiment, cloned variable regions can be mutagenized, and sequences encoding variants with the desired specificity can be selected (e.g., from a phage library; see e.g., Krebber et al., U.S. Pat. No. 5,514,548;

Hoogenboom et al., WO 93/06213, published Apr. 1, 1993)).

Other appropriate inhibitors and promoters can be identified in a suitable assay. For example, the invention pertains to a method of detecting or identifying an inhibitor or promoter of LERK-2-mediated cell adhesion, comprising combining an agent to be tested with a composition comprising a cell expressing LERK-2 and a composition comprising a cell expressing a receptor for LERK-2 (e.g., Nuk), under conditions suitable for binding of LERK-2 to the receptor for LERK-2. The cell adhesion between the cell expressing LERK-2 and the cell expressing a receptor for LERK-2 is detected or measured, and inhibition or promotion of cell adhesion by the agent is indicative that the agent is an inhibitor or promoter, respectively.

In a particular embodiment, cell adhesion between a cell expressing LERK-2 and a cell expressing a receptor for LERK-2 mediates a cellular signalling and/or cellular response (e.g., angiogenesis, inflammatory response, leukocyte migration), and cell adhesion is monitored by detecting or measuring a signalling activity or cellular response of one or both of the cells in response thereto. Signalling events triggered by LERK-2/receptor interaction and LERK-2-mediated cell adhesion, such as induction of rapid and transient increase in the concentration of intracellular (cytosolic) free calcium $[Ca^{2+}]_i$, can be assayed by methods known in the art or other suitable methods (see e.g., Neote, K. et al., Cell, 72: 415–425 1993); Van Riper et al., J. Exp. Med., 177: 851–856 (1993); Dahinden, C. A. et al., J. Exp. Med., 179: 751–756 (1994)).

For example, modulators which can be identified as described herein include modulating antibodies, e.g., antibodies which inhibit or promote LERK-2-mediated cell adhesion. Modulating antibodies can be an antibody or functional antibody fragment which modulates LERK-2-mediated cell adhesion, such as an antibody or fragment which modulates binding of LERK-2 to a receptor for LERK-2. In a particular embodiment, the antibody or functional antibody fragment is an anti-LERK-2 antibody.

Binding inhibition assays can also be used to identify antibodies which bind LERK-2 or a receptor for LERK-2 and inhibit binding of another compound such as a receptor for LERK-2 or LERK-2, respectively, thereby inhibiting LERK-2-mediated cell adhesion. For example, a binding assay can be conducted in which a reduction in the binding of LERK-2 to a LERK-2 receptor (in the absence of an antibody), as compared to binding of LERK-2 to a LERK-2 receptor in the presence of the antibody, is detected or measured. A reduction in the extent of binding in the presence of the antibody is indicative of inhibition of binding by the antibody.

In one embodiment, direct inhibition of the binding of LERK-2 to a receptor for LERK-2 by an inhibitor, e.g., an antibody, is monitored. For example, the ability of an antibody to inhibit the binding of $^{125}$I-labeled LERK-2 to Nuk can be monitored. Such an assay can be conducted using either whole cells (e.g., T cells, or a suitable cell line containing nucleic acid encoding the ligand or receptor) or a membrane fraction from said cells, for instance.

It will be understood that the inhibitory effect of antibodies of the present invention can be assessed in a binding inhibition assay. Competition between antibodies for receptor and/or ligand (LERK-2) binding can also be assessed in the method. Antibodies which are identified in this manner can be further assessed to determine whether, subsequent to binding, they act to inhibit LERK-2-mediated cell adhesion and/or to assess their therapeutic utility.

Chemotaxis assays can also be used to assess the ability of a compound to block binding of LERK-2 to a LERK-2 receptor and/or inhibit LERK-2-mediated cell adhesion. These assays are based on the functional migration of cells in vitro or in vivo induced by a compound. The use of an in vitro transendothelial chemotaxis assay is described by Springer et al. (Springer et al., WO 94/20142, published Sep. 15, 1994, the teachings of which are incorporated herein by reference; see also Berman et al., Immunol. Invest. 17: 625–677 (1988)). Migration across endothelium into collagen gels has also been described (Kavanaugh et al., *J. Immunol.*, 146: 4149–4156 (1991)). Stable transfectants of mouse L1-2 pre-B cells or of other suitable host cells capable of chemotaxis can be used in chemotaxis assays, for example.

Generally, chemotaxis assays monitor the directional movement or migration of a suitable cell (such as a leukocyte (e.g., lymphocyte, eosinophil, basophil)) into or through a barrier (e.g., endothelium, a filter), toward increased levels of a compound, from a first surface of the barrier toward an opposite second surface. Membranes or filters provide convenient barriers, such that the directional movement or migration of a suitable cell into or through a filter, toward increased levels of a compound, from a first surface of the filter toward an opposite second surface of the filter, is monitored. In some assays, the membrane is coated with a substance to facilitate adhesion, such as ICAM-1, fibronectin or collagen. Such assays provide an in vitro approximation of leukocyte "homing".

For example, one can detect or measure inhibition of the migration of cells in a suitable container (a containing means), from a first chamber into or through a microporous membrane into a second chamber which contains an antibody to be tested, and which is divided from the first chamber by the membrane. A suitable membrane, having a suitable pore size for monitoring specific migration in response to compound, including, for example, nitrocellulose, polycarbonate, is selected. For example, pore sizes of about 3–8 microns, and preferably about 5–8 microns can be used. Pore size can be uniform on a filter or within a range of suitable pore sizes.

To assess migration and inhibition of migration, the distance of migration into the filter, the number of cells crossing the filter that remain adherent to the second surface of the filter, and/or the number of cells that accumulate in the second chamber can be determined using standard techniques (e.g., microscopy). In one embodiment, the cells are labeled with a detectable label (e.g., radioisotope, fluorescent label, antigen or epitope label), and migration can be assessed in the presence and absence of the antibody by determining the presence of the label adherent to the membrane and/or present in the second chamber using an appropriate method (e.g., by detecting radioactivity, fluorescence, immunoassay). The extent of migration induced by an antibody agonist can be determined relative to a suitable control (e.g., compared to background migration determined in the absence of the antibody, compared to the extent of migration induced by a second compound (i.e., a standard), compared with migration of untransfected cells induced by the antibody).

In a preferred embodiment, particularly for T cells, monocytes or other cells expressing LERK-2, transendothelial migration is monitored. Such assays are better physiological models, because they more accurately recapitulate in vivo conditions in which leukocytes emigrate from blood vessels toward chemoattractants present in the tissues at sites of inflammation by crossing the endothelial cell layer lining the vessel wall. In addition, transendothelial assays have lower background and as a result a higher signal to noise ratio.

In one embodiment used to test for an antibody inhibitor, a composition comprising cells capable of migration and expressing a receptor for LERK-2 can be placed in the first chamber. A composition comprising LERK-2 or a promoter capable of inducing chemotaxis of the cells in the first chamber (having chemoattractant function) is placed in the second chamber. Preferably shortly before the cells are placed in the first chamber, or simultaneously with the cells, a composition comprising the antibody to be tested is placed, preferably, in the first chamber. Antibodies which can bind receptor and inhibit the induction of chemotaxis, by LERK-2 or promoter, of the cells expressing a receptor for LERK-2 in this assay are inhibitors of receptor function. A reduction in the extent of migration induced by LERK-2 or promoter in the presence of the antibody is indicative of inhibitory activity. Separate binding studies can be performed to determine whether inhibition is a result of binding of the antibody to receptor or occurs via a different mechanism.

In vivo assays which monitor leukocyte infiltration of a tissue, in response to injection of a compound (e.g., antibody) in the tissue, are models of in vivo homing which measure the ability of cells to respond to a ligand or promoter by emigration and chemotaxis to a site of inflammation.

The assays described above, which can be used to assess the inhibitory or promoter effects of test compounds, can be adapted to identify inhibitors and/or promoters of LERK-2-mediated cell adhesion. For example, agents having the same or a similar binding specificity as that of an antibody of the present invention or functional portion thereof can be identified by a competition assay with said antibody or portion thereof. In one embodiment, cells expressing LERK-2 or functional variant thereof (e.g., leukocytes or suitable host cells which have been engineered to express LERK-2 or functional variant encoded by a nucleic acid introduced into said cells) are used in an assay to identify and assess the efficacy of substances which bind LERK-2 or LERK-2 receptors, including inhibitors or promoters of receptor function.

The present invention also pertains to a method for the treatment of angiogenic disease, particularly angiogenesis-sustained solid tumors, in an individual. The term "individual" is defined herein to include animals such as mammals, including, but not limited to, primates (e.g., humans), cows, sheep, goats, horses, dogs, cats, rabbits, guinea pigs, rats, mice or other bovine, ovine, equine, canine, feline, rodent or murine species. As used herein, "angiogenic disease" includes any pathological condition associated with enhanced angiogenesis, that is, a condition which is directly or indirectly supported, sustained or aggravated by increased angiogenesis.

As all solid tumors are dependent on enhanced angiogenesis to grow, the treatment of the invention is generally applicable to any solid tumor; the invention is also useful in the treatment or prevention of metastisis. For example, the methods of the present invention are useful in the treatment of tumors of the prostate, breast, endometrium, lung, colon and kidney, sarcomas, melanomas and skin tumors, including metastasizing tumors. The invention also relates to treatments for psoriasis, rheumatoid arthritis, atherosclerosis, ulcerative colitis, gastric ulcers, corneal graft rejection, corneal neovascularization following injury or infection, diabetic retinopathy, retrolental fibroplasia and neovascular glaucoma, as well as conditions such as hemangioma, angiofibroma of the nasopharynx, avascular necrosis of bone, and psoriasis. The method of the present invention can also be used to inhibit the angiogenesis which accompanies the development of the endometrium, thereby finding use as a contraceptive. In some instances it may be clinically beneficial to enhance or promote angiogenesis in an individual. For example, the process of wound healing requires the neovascularization of newly generated tissue, and a major factor in graft survival is the ability of new vasculature to infiltrate the grafted tissue and connect the tissue to the nutrients and waste removal system provided by the circulatory system of the individual. Enhanced angiogenesis is also useful in the treatment of frostbite to replace the damaged or destroyed capillaries in frostbitten tissue, as well as in recannulization of a thrombis following vascular thrombosis.

Accordingly, the invention pertains to a method of modulating (i.e., inhibiting or promoting) angiogenesis in an individual in need of such therapy, comprising administering a therapeutically effective amount of an agent which inhibits (an inhibitor) or promotes (a promoter) LERK-2-mediated cell adhesion to an individual in need of such therapy. A therapeutically effective amount is an amount sufficient to achieve the desired therapeutic effect, under the conditions of administration, such as an amount sufficient for inhibition or promotion of LERK-2-mediated cell adhesion, and thereby, inhibition or promotion, respectively, of a LERK-2/receptor-mediated process (e.g., an angiogenic response, an inflammatory response or a leukocyte trafficking response).

In one embodiment, a compound which inhibits LERK-2-mediated cell adhesion is administered to inhibit angiogenesis. As used herein, "inhibition" includes any quantitative or qualitative reduction, including prevention and complete absence, relative to the control. In another embodiment, a compound which promotes LERK-2-mediated cell adhesion is administered to promote angiogenesis. As used herein, "promotion" includes any quantitative or qualitative increase relative to the control. For example, the invention pertains to a method of modulating angiogenesis in an individual in need of such therapy, comprising administering an agent which inhibits or promotes LERK-2/Nuk-mediated cell adhesion.

Additionally, the invention relates to a method for modulating the migration of cells, particularly endothelial cells. Cell migration is important to angiogenesis. New capillaries cannot be formed unless the endothelial cells have the ability to migrate to and in the extracellular space. There, they align to form solid cords; formation of a lumen eventually occurs when cords sprouting from adjacent capillaries meet each other.

In another aspect, the present invention provides a method of modulating (i.e., inhibiting or promoting) an inflammatory response in an individual in need of such therapy, comprising administering a therapeutically effective amount of an agent which inhibits or promotes LERK-2-mediated cell adhesion to an individual in need of such therapy. For example, the invention pertains to a method of modulating inflammation in an individual in need of such therapy, comprising administering an agent which inhibits or promotes LERK-2/Nuk-mediated cell adhesion. In one embodiment, a compound which inhibits LERK-2-mediated cell adhesion is administered to inhibit inflammation. As a result, one or more inflammatory processes, such as leukocyte emigration, chemotaxis, exocytosis (e.g., of enzymes) or inflammatory mediator release, is inhibited. For example, leukocytic infiltration of inflammatory sites (e.g., in a delayed-type hypersensitivity response) can be inhibited according to the present method.

In another embodiment, a compound which promotes LERK-2-mediated cell adhesion is administered to promote an inflammatory response, such as leukocyte emigration, chemotaxis, exocytosis (e.g., of enzymes) or inflammatory mediator release, resulting in the beneficial stimulation of inflammatory processes. For example, natural killer cells can be recruited to combat viral infections or neoplastic disease.

A variety of in vivo models of inflammation are available, which can be used to assess the effects of inhibitors or promoters of LERK-2-mediated cell adhesion in vivo as therapeutic agents, including a sheep model for asthma (see e.g., Weg, V. B. et al., *J. Exp. Med.*, 177: 561 (1993)), a rat delayed type hypersensitivity model (Rand, M. L. et al., *Am. J. Pathol.*, 148: 855–864 (1996)), or other suitable models.

Inflammatory diseases or conditions, including chronic diseases, of humans or other species which can be treated with inhibitors of LERK-2-mediated cell adhesion, include, but are not limited to allergic diseases and conditions, including systemic anaphylaxis or hypersensitivity responses, drug allergies (e.g., to penicillin, cephalosporins), insect sting allergies; inflammatory bowel diseases, such as Crohn's disease, ulcerative colitis, ileitis and enteritis; vaginitis; psoriasis and inflammatory dermatoses such as dermatitis, eczema, atopic dermatitis, allergic contact dermatitis, urticaria; vasculitis (e.g., necrotizing, cutaneous, and hypersensitivity vasculitis); spondyloarthropathies; scleroderma; respiratory allergic diseases such as asthma, allergic rhinitis, hypersensitivity lung diseases, hypersensitivity pneumonitis, and interstitial lung diseases (ILD) (e.g., idiopathic pulmonary fibrosis, or ILD associated with rheumatoid arthritis, or other autoimmune conditions).

Other disease and conditions which can be treated by the methods of this invention include autoimmune diseases, such as arthritis (e.g., rheumatoid arthritis, psoriatic arthritis), multiple sclerosis, systemic lupus erythematosus, myasthenia gravis, diabetes, including diabetes mellitus and juvenile onset diabetes, glomerulonephritis and other nephritides, autoimmune thyroiditis, Behcet's disease; graft rejection (e.g., in transplantation), including allograft rejection or graft-versus-host disease; and other diseases or conditions in which undesirable inflammatory responses are to be inhibited can be treated, including, but not limited to, atherosclerosis, cytokine-induced toxicity, myositis (including polymyositis, dermatomyositis).

Also suitable for treatment as described herein are cancers, particularly those with leukocytic infiltration of the skin or organs such as cutaneous T cell lymphoma (e.g., mycosis fungoides); diseases in which angiogenesis or neovascularization plays a role, including neoplastic disease, retinopathy (e.g., diabetic retinopathy), and macular degeneration; and infectious diseases, such as bacterial infections and tuberculoid leprosy, and especially viral infections. Inhibitory compounds described herein can also be administered to inhibit angiogenesis as an antitumor therapy in conjunction with anti-tumor chemotherapeutic agents known in the art.

Inhibitors and promoters of LERK-2-mediated cell adhesion can be used in the described methods. Appropriate inhibitors and promoters can be identified in a suitable assay, such as assays described herein, and further assessed for therapeutic effect. For example, antibodies of the present invention, including mAb 2A1 and 4A1, as well as functional antibody fragments of mAb 2A1 and 4A1, and antibodies which can compete with monoclonal antibodies 2A1 and 4A1, can be used in the method to inhibit LERK-2-mediated cell adhesion, thereby inhibiting angiogenesis and/or inflammation.

The present invention also relates to preparations for use in the modulation of angiogenesis and inflammation, the treatment of angiogenic diseases and inflammatory disorders, and the modulation of leukocyte trafficking, the preparation including an inhibitor or promoter of LERK-2-mediated cell adhesion, together with a physiologically acceptable carrier and optionally other physiologically acceptable adjuvants.

According to the method, a therapeutically effective amount of one or more agents (e.g., a preparation comprising an inhibitor or promoter of LERK-2-mediated cell adhesion, particularly LERK-2/Nuk-mediated cell adhesion, can be administered to an individual by an appropriate route, either alone or in combination with another drug.

A variety of routes of administration are possible including, but not limited to, oral, dietary, topical, parenteral (e.g., intravenous, intraarterial, intramuscular, subcutaneous injection), and inhalation (e.g., intrabronchial, intranasal or oral inhalation, intranasal drops) routes of administration, depending on the agent and disease or condition to be treated. For respiratory allergic diseases such as asthma, inhalation is a preferred mode of administration.

Formulation of an agent to be administered will vary according to the route of administration selected (e.g., solution, emulsion, capsule). An appropriate composition comprising the agent to be administered can be prepared in a physiologically acceptable vehicle or carrier. For solutions or emulsions, suitable carriers include, for example, aqueous or alcoholic/aqueous solutions, emulsions or suspensions, including saline and buffered media. Parenteral vehicles can include sodium chloride solution, Ringer's dextrose, dextrose and sodium chloride, lactated Ringer's or fixed oils, for instance. Intravenous vehicles can include various additives, preservatives, or fluid, nutrient or electrolyte replenishers and the like (See, generally, *Remington's Pharmaceutical Sciences*, 17th Edition, Mack Publishing Co., PA, 1985). For inhalation, the agent can be solubilized and loaded into a suitable dispenser for administration (e.g., an atomizer, nebulizer or pressurized aerosol dispenser).

Furthermore, where the agent is a protein or peptide, the agent can be administered via in vivo expression of the recombinant protein. In vivo expression can be accomplished via somatic cell expression according to suitable methods (see, e.g. U.S. Pat. No. 5,399,346). In this embodiment, nucleic acid encoding the protein can be incorporated into a retroviral, adenoviral or other suitable vector (preferably, a replication deficient infectious vector) for delivery, or can be introduced into a transfected or transformed host cell capable of expressing the protein for delivery. In the latter embodiment, the cells can be implanted (alone or in a barrier device), injected or otherwise introduced in an amount effective to express the protein in a therapeutically effective amount.

The present invention will now be illustrated by the following Examples, which are not intended to be limiting in any way. The teachings of all references cited herein are incorporated herein by reference.

EXAMPLES

Methodology

RNA Isolation and Selection of Message

Total RNA was isolated from both primate (macaque) and human (both histologically normal and inflamed ileal nodes from a patient with Chrohn's disease) mesenteric lymph nodes or tissue culture cells by use of the cesium trifluoroacetate (CsTFA™) reagent from Pharmacia (Catalog #17-087-02). Tissue was first snap frozen in liquid nitrogen and subjected to dounce homogenization in a solution consisting of 5.5 M guanidinium thiocyanate, 25 mM sodium citrate, 0.5% sodium laurel sarcosine and 0.2 M 2-mercaptoethanol, while tissue culture cells ($1-5 \times 10^8$) were washed once in phosphate buffered saline (PBS) and homogenized by pipetting. A clarified lysate was then layered on a cushion of CsTFA™ and total RNA was pelleted by centrifugation for 20 hours at 30,000 RPM.

mRNA was selected by the polyATract mRNA isolation system from Promega. The system uses a biotinylated oligo (dT) primer to hybridize (in solution) to poly A tails of eukaryotic messages. The hybrids are captured and washed at high stringency using streptavidin coupled to paramagnetic particles and a magnetic separation stand. mRNA was selected by a single purification in this system and the yields ranged from 1–2% of the total RNA yield. The integrity of both the total and mRNA was analyzed by gel electrophoresis and ethidium bromide staining.

cDNA Synthesis and Library Construction cDNA was synthesized using the Superscript™ lambda system (catalog #18256-016) in conjunction with either the IZiplox™ vector (catalog #19643-014) or the pSV-SPORT-1 vector (catalog #15388-010) from GibcoBrl with the following modifications from the standard protocol. cDNA was labeled only in the first or second strand (but not both) with $\alpha^{32}$p dCTP and crude estimates of quantity were made by inspection of ethidium bromide staining of aliquots of cDNA fractions.

Macaque Expression Library: The size fractionation procedure was also modified slightly for construction of the macaque expression library to ensure large (>1.5 kb) inserts. After one round of fractionation, only the first (largest) fraction of cDNA was saved and the remaining fractions were pooled and subjected to a subsequent round of fractionation. The top fraction from the next round was pooled with the top fraction from the previous round and the second fraction from this round was also used. These two fractions were precipitated and put into ligations with the pSV-SPORT-1 vector, and a fraction of each ligation was transformed into electrocompetent DH10B bacteria (Gibco) to estimate both the titer of the library and the average insert size. Estimates from ligation of only the top largest cDNA fraction revealed the potential of making up 2.4 million independent clones with an average insert size of 1.9 kb and a median size of 2 kb.

The actual library screened consisted of 150,000 independent clones which were plated at a density of 1,500 clones/plate on 100 LB agar plates (to generate 100 pools of 1,500 clones/pool) with ampicillin at 50 µg/ml and grown overnight at 37° C. For purification of individual pools, each plate was overlayed with approximately 2 ml of luria broth (LB), the colonies were scraped off each plate with a standard tissue culture cell scraper, and bacterial suspensions were transferred to microfuge tubes. Prior to purification, a glycerol stock was generated from each pool. Plasmid DNAs were purified by use of QIAprep spin columns (QIAGEN) according to manufacturer's instructions.

Transfections and Adhesion Assays

CHO/P cells were seeded into 24-well plates approximately 24 hours prior to transfection at a density of 40,000 cells/well. DNAs were transiently transfected using the LiptofectAMINE™ reagent (GIBCO catalog #18324-012), essentially following the recommended protocol with further optimization for 24-well plates as follows: 200 ng of DNA (representing either a plasmid pool or purified control DNAs) was diluted to 20 µl with Opti-MEM 1 reduced serum media (GIBCO) and diluted into 20 µl of a mixture that consists of 18 µl Opti-MEM 1 and 2 µl of lipofectamine reagent. This liposome mixture was then incubated for approximately 30 minutes at ambient temperature, after which 200 µl of Opti-MEM 1 was added, and the entire mixture was then overlayed onto a well of CHO/P cells and returned to the incubator. After a 2.5 hour incubation, 240 μl of MEM-α (Gibco) media with 20% fetal calf serum (FCS) was added to each well, and the cells were incubated for an additional 18–24 hours. The media was then changed to standard MEM-α with 10% FCS, and the adhesion assay was performed approximately 20–24 hours later.

For the adhesion assays in the expression cloning screen, the murine T cell lymphoma TK1 was used to detect cDNAs mediating cell adhesion. TK1 cells were resuspended at a density of 2×10$^6$/ml in an assay buffer which consisted of HBSS (without Ca$^{++}$ and Mg$^{++}$) supplemented with 2% bovine calf serum, 20 mM HEPES pH 7.3, 2 mM Mg$^{++}$ and 2 mM Ca$^{++}$. Each well transfected with a DNA pool was pre-incubated with 0.25 ml of a combined supernatant containing monoclonal antibodies to both human VCAM-1 (2G7; Graber et al., *J. Immunol.* 145:819 (1990)) and murine MAdCAM-1 (MECA-367; Streeter et al., *Nature* 331:41 (1988)) in order to eliminate adhesion mediated by VCAM-1 (which is expressed at high levels in primate lymph nodes) or any potential contaminating murine MAdCAM-1 expression plasmids. After incubation at 4° C. for 15 minutes, 0.25 ml of the TK1 cell suspension (5×10$^5$ TK1 cells) was added to each well and incubation on a rocking platform was continued for an additional 30 minutes at 4° C. Plates were washed by gently inverting in a large beaker of phosphate buffered saline (PBS) followed by inversion in a beaker of PBS with 1.5% gluteraldehyde for fixation for a minimum of 1 hour. Wells were then examined microscopically (10×objective) for rosseting of TK1 cells mediated by the pools of cDNA clones.

The following plasmids were utilized for functional adhesion assays: pSV-SPORT-1 (GIBCO) or pcDNA3 (Invitrogen) controls, murine MAdCAM-1 in pCDM8 (pCDMAD-7), seven domain human VCAM-1 in pcDNA3 (pCD3VCAM), and human MAdCAM-1 in pcDNA3 (pCDhuMAd4). Monoclonal antibodies used were anti-murine MAdCAM-1 MECA-367, anti-human VCAM-1 2G7, anti-murine α4β7 DATK32, anti-murine β7 FIB 504, anti-human α4β7 ACT-1, anti-human integrin β1(CD29) from Becton Dickinson (catalog #550034) and murine IgG1 and rat IgG2A as irrelevant controls (Sigma, St. Louis, Mo.).

Functional adhesion assays used the following cell lines: the murine T cell lymphoma TK1, RPMI 8866, a human B cell lymphoma which expresses α4β7 (and not α4β1) and JURKAT, a human T cell line which expresses α4β1 (and not α4β7). Assays were performed by transient transfection of plasmids encoding LERK-2 (also known as Ephrin B2), various species of MAdCAM-1, human VCAM-1, and control plasmids into CHO/P cells as described above with the following exception: as several wells were to be transfected for antibody inhibition studies, a master liposome mix with multiples of the wells to be transfected was first made for each plasmid. This ensured that the same liposome mixture was transfected into each well. On the day of the assay, monoclonal antibodies were incubated with cells at 20 μg/ml at 4° C. for 15 minutes prior to the start of the assay. Supernatants of 2G7, MECA 367 and DATK 32 were all used either neat or diluted 1:2. Assays were fixed as described above and quantitated by counting both lymphocytes and CHO cells in a field at 20×magnification. For each assay, the number of lymphocytes bound per CHO/P cell was averaged as a minimum of four fields with standard error. Results in each case are from one of three experiments performed with similar results.

Purification of Primate Clones

Pools yielding one or more TK1 rosettes were further subfractionated by the following protocol: DNA representative of a positive pool was retransformed into DH10B and plated on 96 plates at a density of approximately 200 colonies/plate. Nitrocellulose filters were used to generate replica plates, and one set of each plate was then subjected to DNA purification and subsequent adhesion assays as described above. A replica plate representative of a positive pool was then further subfractionated into pools of 5 colonies which were replica plated and grown overnight in LB AMP media. After one more round of DNA purification and adhesion assays, individual clones were then grown up and the clones conferring adhesion of the TK1 cells were identified.

DNA Sequencing

Plasmids used in sequencing were as follows: The entire macaque LERK-2 cDNA was first isolated in the original vectors pSV-SPORT-1 and pZL1 (rescued from IZiplox™), respectively. Based on restriction mapping, subcloned fragments into Stratagene's Bluescript® vectors were also made to facilitate sequencing from internal regions of the cDNAs. After initial sequence analysis of these clones, oligonucleotide primers were made to complete the sequence. Overlapping sequence of both strands was obtained to ensure fidelity of the reported sequence. Sequence analysis utilized the SEQUENASE™ 7-deaza-dGTP DNA sequencing kit with SEQUENASE version 2.0 T7 DNA polymerase (United States Biochemical) and 35SdCTP (Amersham Life Science and New England Nuclear). Sequences were entered and analyzed using the Lasergene system (DNAstar Inc.).

Sequence alignments were performed by the Clustal method (part of the Lasergene program) using a gap penalty of 10 and a gap length penalty of 10. Pairwise alignment parameters were: ktuple=2, gap penalty-5, window=4 and diagonals saved=4

Northern Blot Analysis

Northern blots used were human multiple tissue northerns I and II (commercially prepared by Clontech). Blots were pre-hybridized at 68° C. for 1 hour in ExpressHyb (Clontech). cDNA's were labeled with α$^{32}$P-dCTP by priming with random hexamers. Hybridization was performed at 68° C. for 1 hour in ExpressHyb with denatured probe at a concentration of 2×10$^6$ CPM/ml. Blots were then washed for 20 minutes in 2×SSC, 0.05% SDS at room temperature, followed by high stringency washes at 50° C., 60° C, or 65° C. in 0.1×SSC, 0.1% SDS for 20 minutes per wash and exposed to Kodak XAR film with an intensifying screen.

Stable LERK-2 Transfectants

The mouse L1-2 cell line is derived from a pre-B lymphoma, and was obtained from Dr. Eugene Butcher (Stanford University, Stanford, Calif.). The gene encoding the macaque cDNA for LERK-2 was subcloned into the pcDNA3 vector (Invitrogen), linearized by digestion with the restriction enzyme ScaI (Gibco), and transfected by the following protocol: L1-2 cells were grown to a density of approximately 10$^6$/ml. Either 50, 25 or 12.5 million cells were washed in HBSS and then resuspended in 0.8 ml of a buffer consisting of Hanks balanced salt solution supplemented with 20 mM HEPES, pH 7.05. A solution consisting of 20 μg of linearized plasmid, 500 μg of tRNA and HBSS to bring the final volume to 200 μl was added to the cell suspension to bring the total volume to 1 ml. After a 10-minute incubation at room temperature, the cell/DNA mixture was transferred to an electroporation cuvette (BioRad, Richmond, Calif.) and electroporated at 250 volts, 960 mF in a BioRad gene pulser. Following another 10-minute incubation, the cells were diluted to 25 ml in standard L1-2 growth media (RMPI 1640, 10% Hyclone fetal bovine serum, Penicillin/Styreptomycin (50 U/ml [Gibco]) and L Glutamine (0.29 mg/ml [Gibco])) and returned to the incubator. Forty-eight hours later, the cells were pelleted by centrifugation and resuspended in 50 ml of L1-2 media supplemented with G418 (Genticin [Gibco]) at 0.8 mg/ml. Dilutions of the cell suspension were plated in 96-well microtiter plates and single colonies were grown up analyzed for expression of LERK-2.

Clones expressing LERK-2 could be detected by aggregation with TK1 cells. L1-2 (non-transfected cells) and TK1 cells both grow as single cell suspensions. Surface expression of LERK-2 is inferred by its ability to mediate aggregation by virtue of its interaction with the putative EPH receptor in on TK1 cells (which we now know is Nuk/EphB2). RNA was prepared from L1-2 lines that mediated significant aggregation, and RNA PCR confirmed that these lines did in fact contain message for LERK-2; as a control, L1-2 cells which did not aggregate were negative by this PCR analysis.

CHO cells stably transfected with LERK-2 cDNA were prepared as described above with the following exceptions. Media for CHO cell growth was α-MEM with deoxyribonucleosides (Gibco) and 10% fetal calf serum (Gibco) and Penicillin/Streptomycin (50 U/ml [Gibco]) and L Glutamine (0.29 mg/ml [Gibco]). Selection media consisted of the same media with 0.55 mg/ml G418 (Gibco). Single clones were grown up and analyzed for their ability to mediate adhesion of TK1 cells. Using this criteria, a line called CHO5C2 was established.

Monoclonal Antibodies

Monoclonal antibodies against primate LERK-2 were generated by immunizing C57BL/6 mice with L1-2 LERK-2 transfectants. Mice were immunized intraperitoneally with 10 million cells, resuspended in HBSS 3 times at two-week intervals, and a final immunization was injected intravenously.

A successful fusion was performed which generated approximately 5,000 hybridomas. Four days after the final intravenous injection, the spleen was removed and a single cell suspension was prepared in serum-free DMEM media. These cells were fused with the fusion partner SP2/0, according to the method of Galfre et al. (*Nature* 299:550–552 (1977)). 20 ml of spleen cells and 20 ml of SP2/0 cells were combined, spun at 800 g for 5 minutes, and the media was aspirated. A solution of 50% polyethylene glycol 1500 (PEG 1500) (Boehringer Mannheim, Indianapolis, Ind.) prewarmed to 37° C. was added to the cell pellet over 2 minutes, followed by 10 ml of DMEM media over 3 minutes. The cell suspension was spun at 600 g for 3 minutes and the supernatant removed. The pellet was resuspended gently in DMEM media containing 20% fetal calf serum, 2 mM L-glutamine, 100 U/ml penicillin, 100 μg/ml streptomycin sulfate, and HAT selection media (Sigma). Cells were plated into 10 96-well flat bottom microtiter plates at 200 μl/well.

Ten days after the fusion, supernatants from the wells were screened for reactivity against CHO LERK-2 transfectants with the CHO5C2 line as a positive control using a flourescently-labeled (FITC) anti-mouse antibody (Jackson Labs). Several antibodies were selected for strong reactivity against the CHO LERK-2 transfectants. The putative positive antibodies were then screened in a plus minus screen using non transfected CHO cells as a negative control. Two antibodies, designated 4A1 and 2A1, were confirmed as anti LERK-2 mAbs.

These supernatants were subsequently screened for their ability to block adhesion of TK1 cells to CHO LERK-2 transfectants, and both mabs could inhibit adhesion of TK1 cells to LERK-2 transfectants. Inhibition experiments were performed essentially as described for supernatants above. These two blocking hybridomas were subcloned using limiting dilution.

The isotype of the two mAbs 2A1 and 4A1 was determined to be IgG2A and IgG1, respectively, by the SBA Clonotyping System/HRP (Southern Biotechnology Associates, Inc.). Maxisorb plates were first coated with a trapping antibody, goat anti-mouse Ig, at 5 μg/ml overnight. The plates were then washed 3 times with PBS/Tween and blocked with 1% BSA for 1 hour at room temperature. After another 3 washes with PBS/Tween, antibodies to be tested and purified isotype standards were added at 100 μg/ml and incubated for 2 hours at room temperature. Then the plates were washed and the mAbs and isotype standards were incubated with a variety of HRP-conjugated anti-isotype antibodies for 1 hour at room temperature followed by detection with OPD substrate.

FACS Analysis

100 μl of whole blood or cell suspensions were added to tubes containing specific (4A1) or irrelevant (IgG1, MOPC21, Sigma, St. Louis, Mo.) primary antibodies in blocking solution to a final concentration of 10 μg/ml. Cell suspensions were incubated at 4° C. for 20 minutes, washed twice with PBS and subsequently incubated with secondary antibody (goat anti mouse-PE, Jackson Immunoresearch, West Grove, Pa.) at a final concentration of 10 mg/ml in blocking solution at 4° C. for 15 minutes. Subsequently, 2 ml of FACS-lysis solution (Becton-Dickinson) was added, and tubes were incubated for 10 minutes at room temperature. Following two final PBS washes, cells were resuspended in 300 ml PBS with 1% fetal calf serum and stored at 4° C. until analyzed.

FACS analysis: Two-color analysis was performed on a Becton Dickinson FACScan flow cytometer. Gating for lymphocytes and granulocytes was based upon forward and side scatter characteristics. For each sample, a minimum of 10,000 cells was counted.

Results

FACS Analysis

Figure 1B:
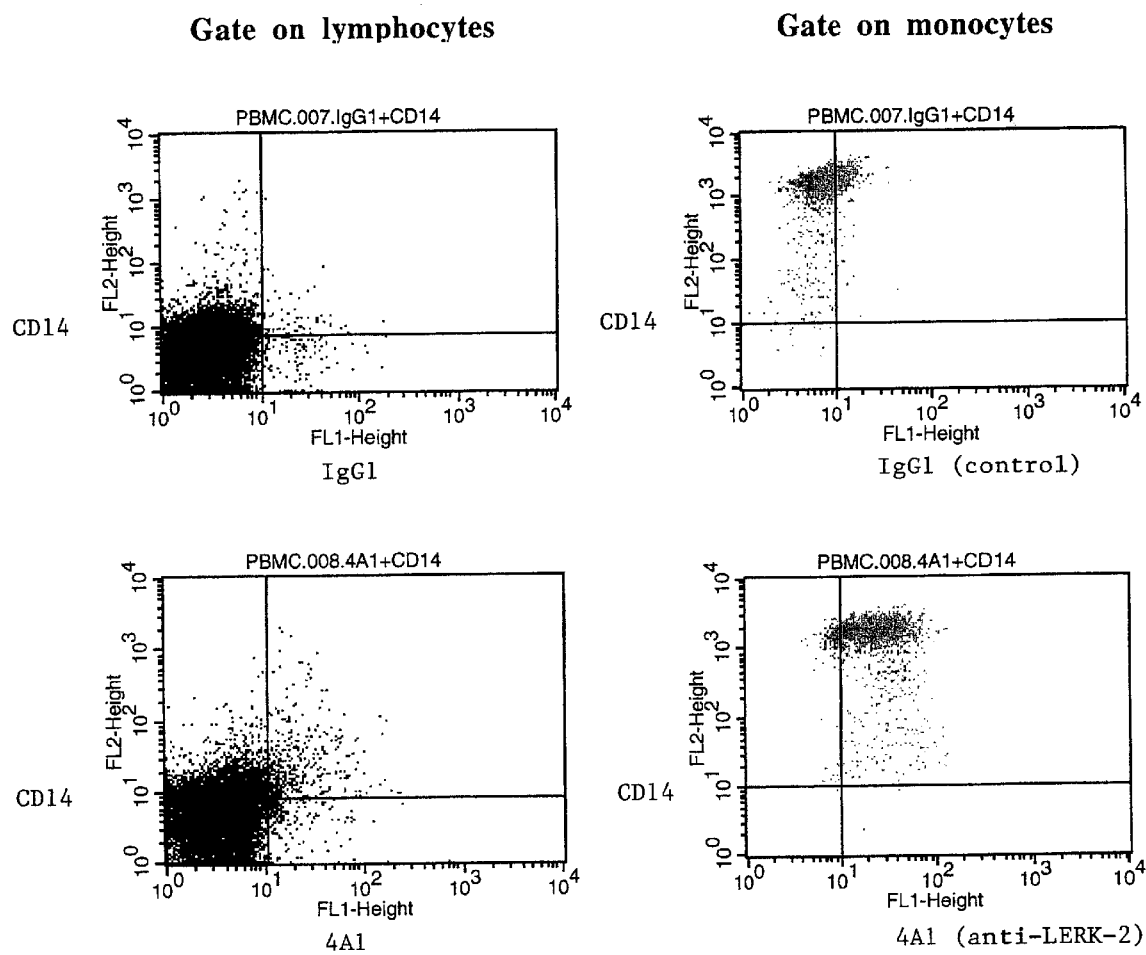
Figure 1C:
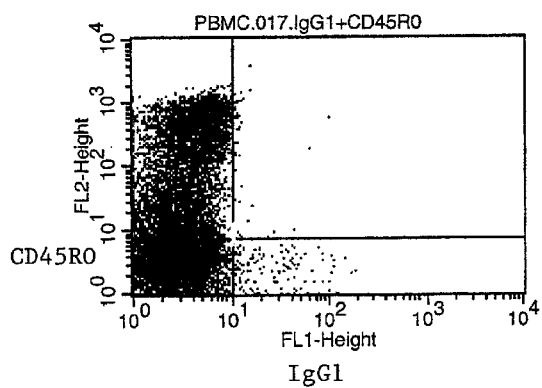
Figure 1C:
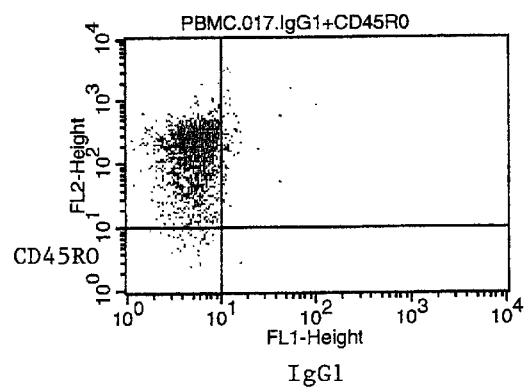
Figure 1C:
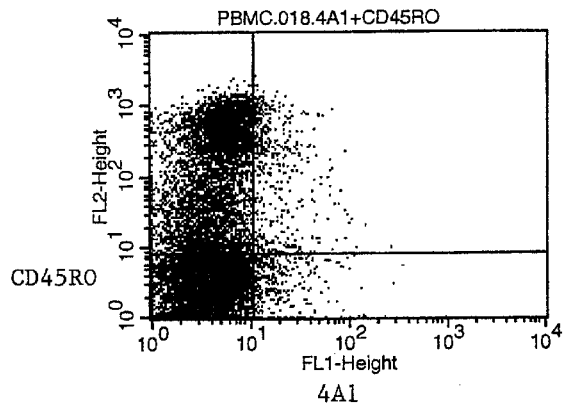
Figure 1C:
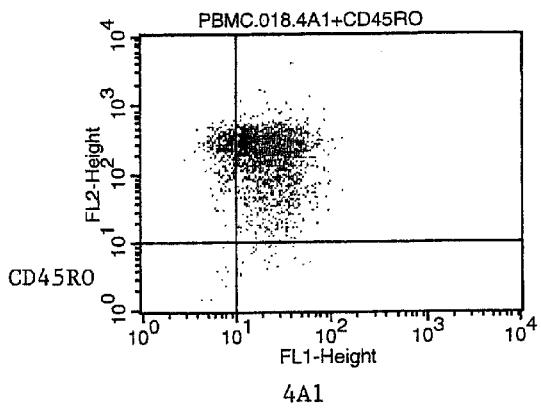

The two anti-LERK-2 mAbs were examined for cross reactivity to human LERK-2 by FACS analysis of human umbilical vein endothelial cells (HUVECs) in the presence or absence of TNF-α. While the 2A1 mAb failed to react, 4A1 did react and was slightly induced by a both 4 and 24 hour incubation with TNF-α. This is consistent with the results of Beckmann et al. (*EMBO J.* 13:3757–3762 (1994)) which showed expression of LERK-2 RNA in northern blots made from TNF-α-stimulated HUVECS The mAb 4A1 was also used to investigate the expression of LERK-2 on leukocytes by FACS analysis. Peripheral blood mononuclear cells (PBMCs) were isolated from human blood using Ficoll. LERK-2 expression on subsets of PBMCs were examined by 2-color staining using both 4A1 and another marker for a subset of leukocytes. It was discovered that LERK-2 is highly expressed on monocytes/macrophages (CD14 positive cells). Some levels of expression were also seen on lymphocytes. The T cell subsets that are positive for LERK-2 include CD4+, CD8+, and CD45RO+ (FIGS. 1A–C).

Figure 2A:
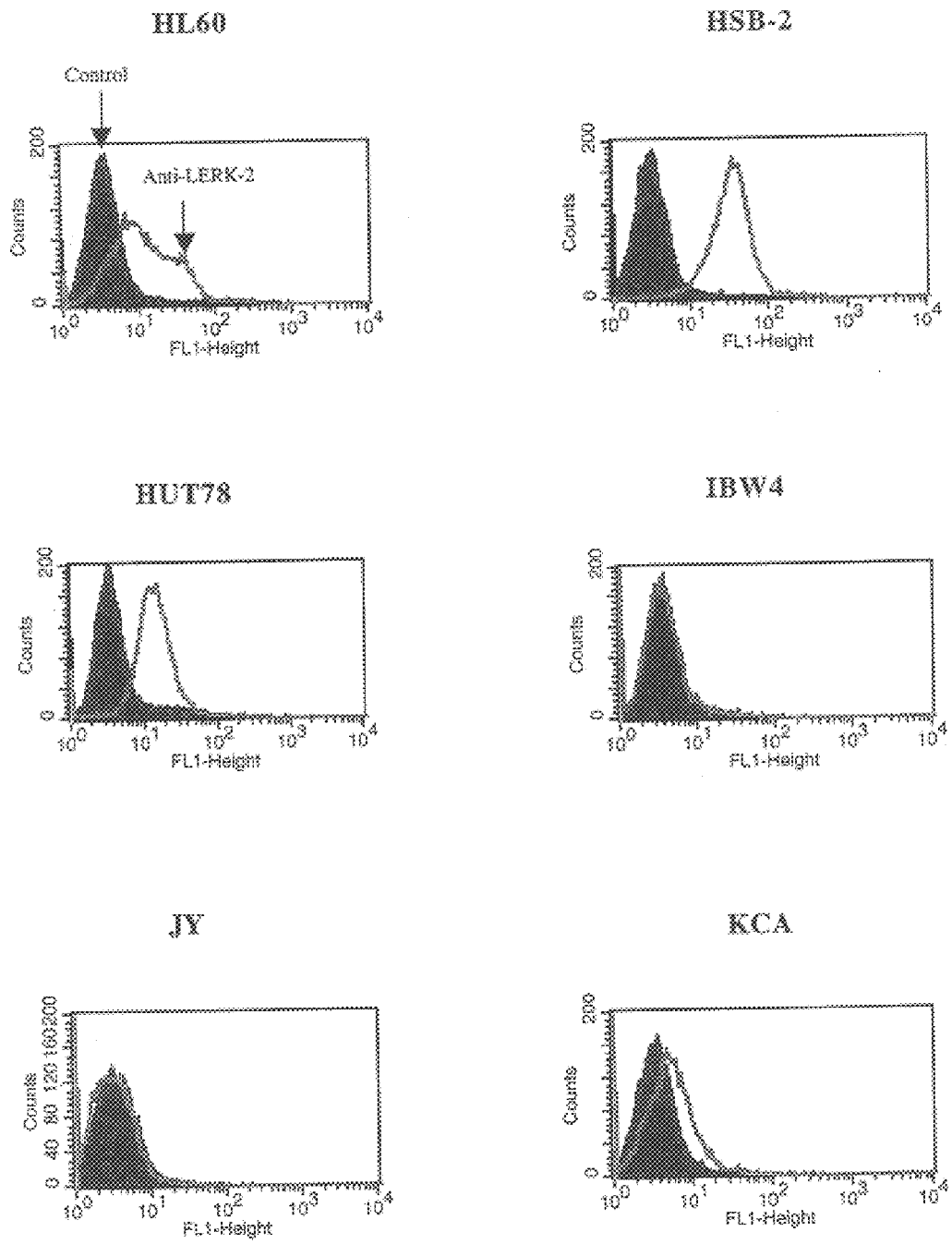
FIGS. 2A and 2B show the results of FACS analysis of the expression of LERK-2 on leukocyte subsets using 4A1 as a staining reagent. Myelomonocytic cell lines including THP-1 and the T cell lines HuT 78 and HSB-2 are brightly positive for LERK-2. Some B cell lines express lower levels of LERK-2, including CA, RAMOS and RAJI.
Figure 2B:
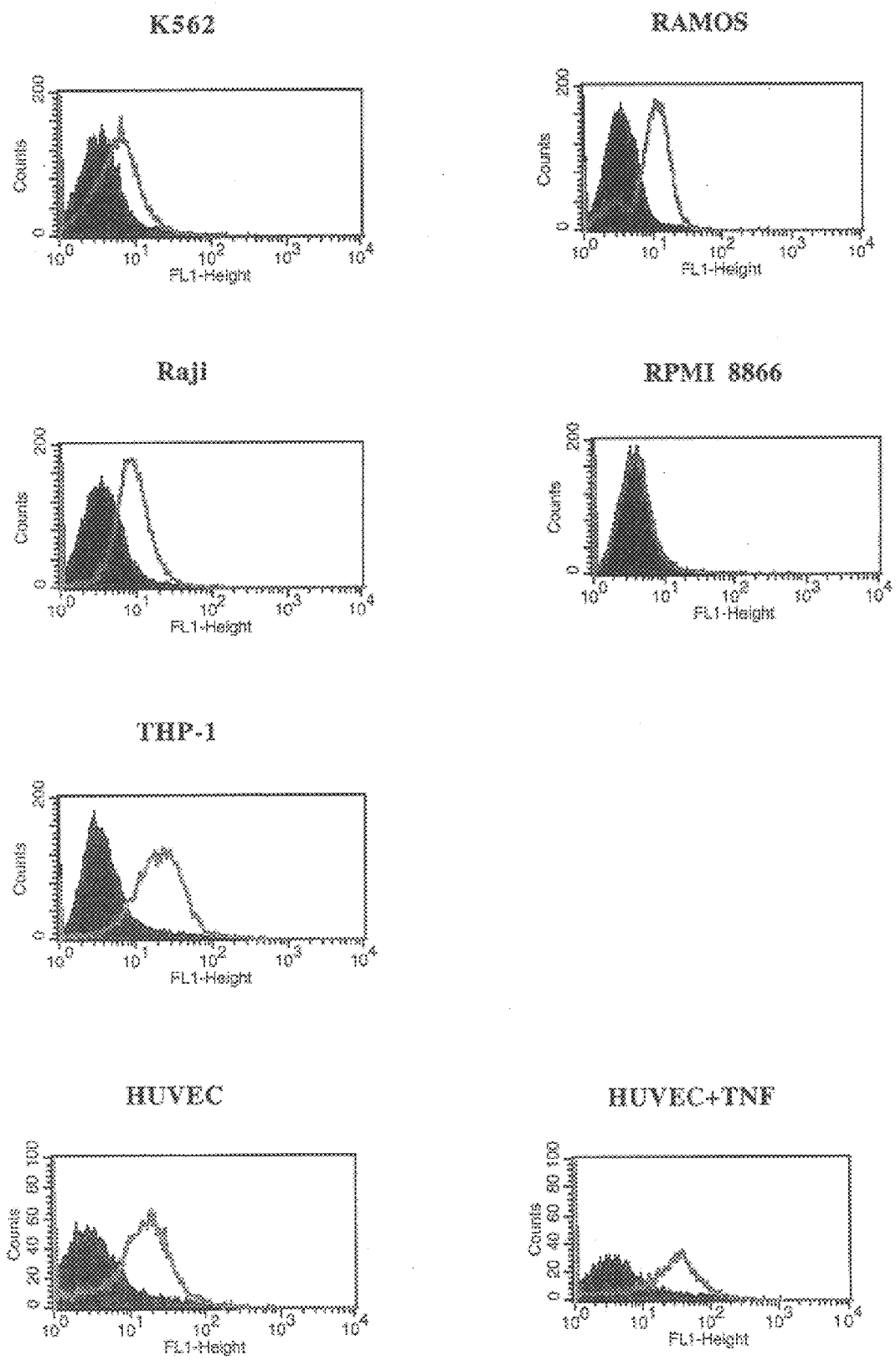

To further confirm the expression of LERK-2 on leukocyte subsets, a variety of monocytic and lymphocytic cell lines were studied by FACS using 4A1 as a staining reagent. The cell lines include HL60, HSB-2, HUT78, IBW4, JY, KCA K562, RAMOS, Raji, RPMI8866, and THP-1 cells. Among these cell lines, THP-1 and HSB-2 express a high level of LERK-2. HL60, HUT78, KCA, K562, RAMOS, and Raji express moderate levels of LERK-2, while IBW4, JY and RPMI do not express LERK-2 by this FACS analysis (FIGS. 2A–B). This result, showing the high level expression of LERK-2 on a monocytic cell line (THP-1) and a lymphocytic cell line (HSB-2), is consistent with the expression pattern on PBMC.

Figure 3:
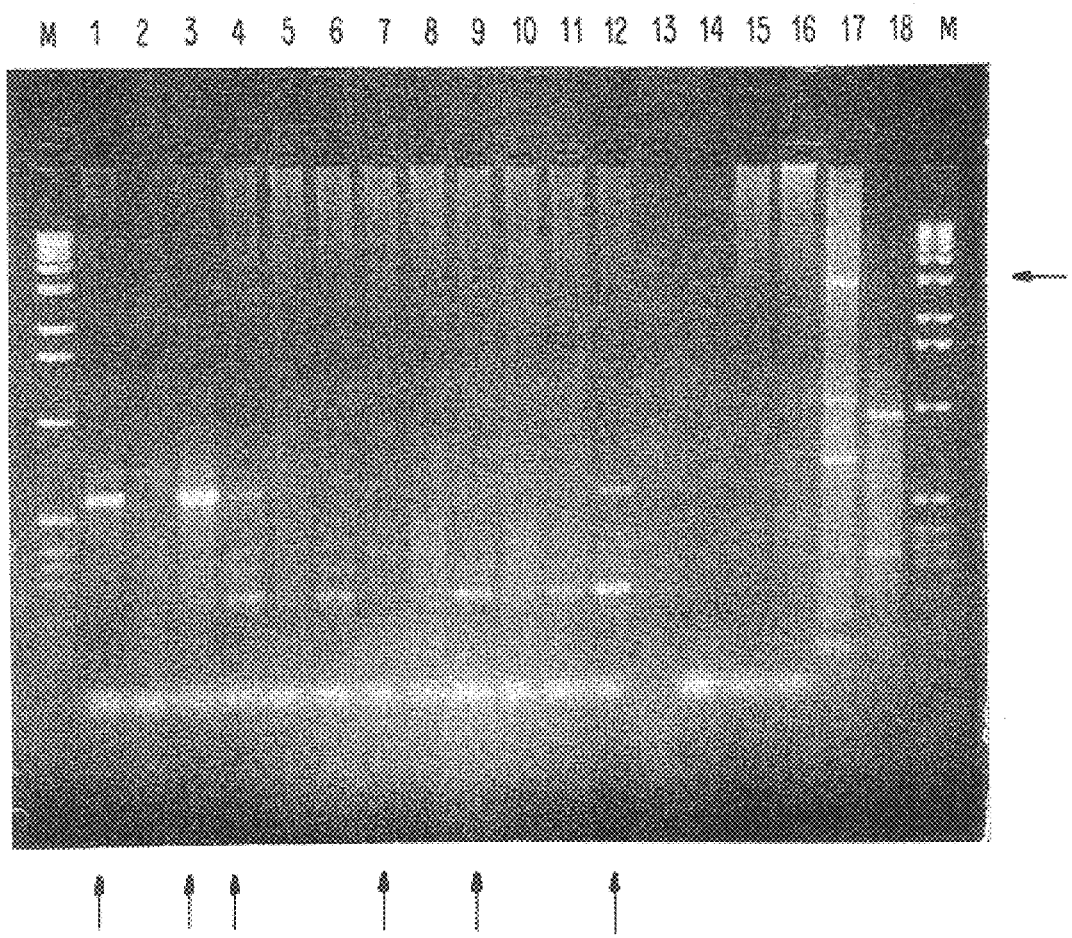
FIG. 3 shows the results of PCR analysis of various cell lines for expression of LERK-2. Lane M=1kb ladder; lane 1=L1-2 20H9; lane 3=PBMC; lane 4=HSB-2; lane 5=IBW-4; lane 6=JY; lane 7=K562; lane 8=KCA; lane 9=Raji; lane 10=RAMOS; lane 11=RPMI 8866; lane 12=THP-1; lane 13=No DNA; lane 14=pAW109; lane 15=HL60; lane 17=TK1 5'Nuk1+3'; lane 18=Tk1 3'Nuk1+3'. Results indicate that cells which are positive for LERK-2 expression by FACS analysis can also specifically amplify a 600 base pair DNA fragment by RNA PCR with LERK-2-specific primers. Positive results are seen in lanes 1 (L1-2 LERK-2 transfectants), 3 (peripheral blood mononuclear cells), 4 (HSB-2), 7 (K562), 9 (RAJI), 10 (RAMOS) and 12 (THP-1). Intensity of the signal closely parallels the intensity of the staining observed by FACS analysis.

The expression of LERK-2 on PBMCs and leukocyte cell lines was confirmed by RT-PCR (FIG. 3). Whole cell polyadenlylated RNA was isolated from PBMC and the leukocyte cell lines used in the FACS analysis using Oligotex Direct mRNA Isolation Kit (QIAGEN). Cells were lysed and the lysates were incubated with oligo(dT)n-coated latex beads to select for polyA+ RNA. The Oligotex beads were wash and polyA+ RNA was eluted from the beads. Reverse transcription (RT) was performed in the presence of MuLV reverse transcriptase, DNTP, Rnase inhibitor, Oligo(dT)$_{16}$, and appropriate polyA+ RNA as template. The reaction was carried out at 42° C. for 1 hour followed by heat inactivation of the enzyme. Polymerase chain reaction (PCR) was performed using a pair of primers specific for LERK-2, the forward amplification primer 5'-GCCCCCGAGCAGAAGCA-3' (SEQ ID NO: 1) and the reverse amplification primer 5'-CAGGAAGATGATGATGAGCAG-3' (SEQ ID NO: 2), in the presence of the RT product. PCR product specific for LERK-2 (600 bp) was obvious in all lines that were brightly positive for LERK-2 including PBMC, THP-1, and HSB-2 cells.

Construction of LERK-2-Ig Chimera and FACS Analysis

Figure 4:
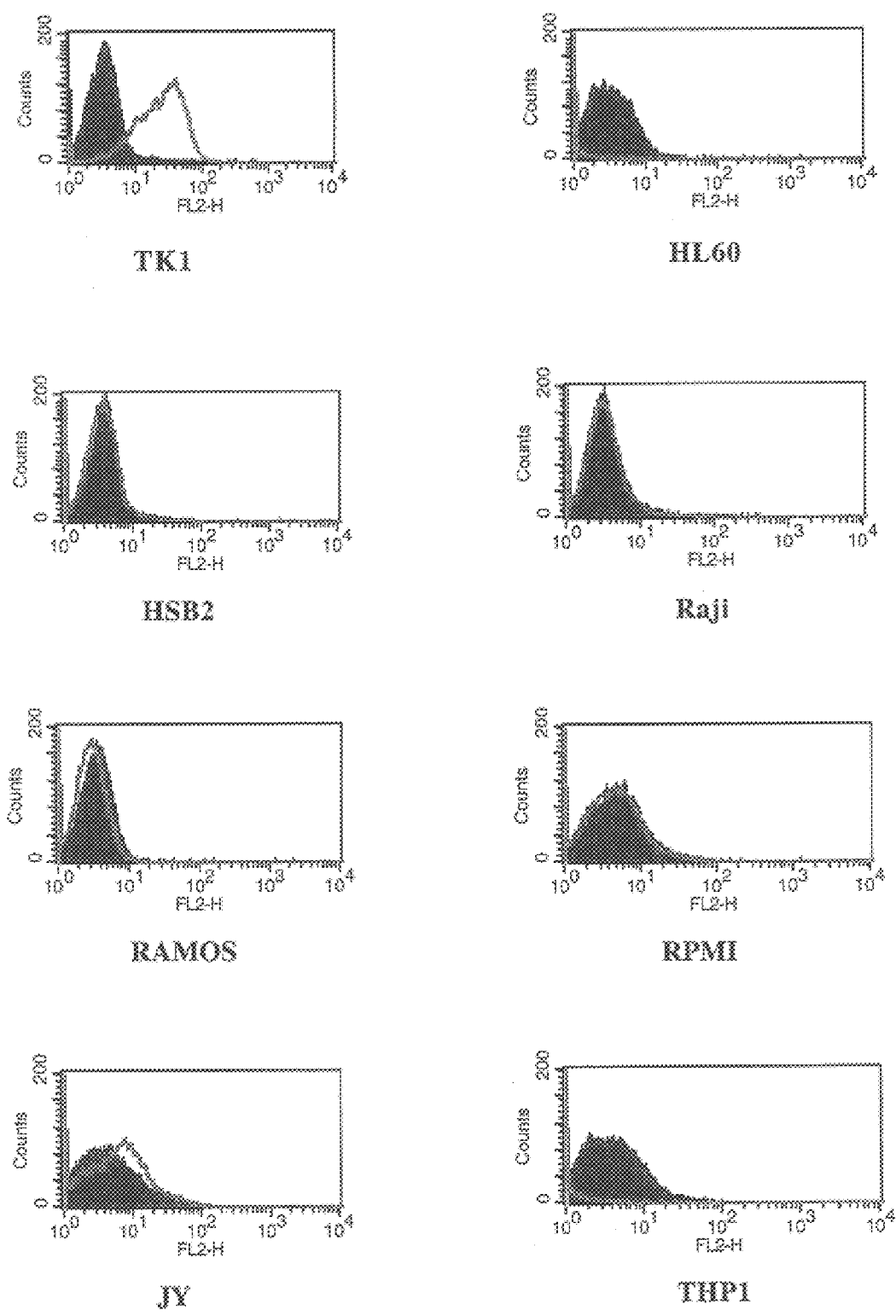
FIG. 4 show the results of FACS analysis using a LERK-2 Ig chimera. These results indicate that TK1 cells express a receptor for LERK-2.

A chimera containing the ectodomain of LERK-2 and the Fc domain of human IgG1 was constructed as described previously (Tidswell et al., *J. Immunol* 159:1497–1505 (1997)) using the forward amplification primer 5'-GGAGCTTCCACCATGGCTCGGCCTGGGCAG-3' (SEQ ID NO: 3) and the reverse amplification primer 5'-GGACTAGTGCCACCTTTGAGTTGAAGAAG-3' (SEQ ID NO: 4) to isolate the LERK-2 ECD. The construct was transiently transfected into CHO-P cells using Lipofectamine (GIBCO), and the supernatant of the transfected cells was harvested. This supernatant was used as a FACS reagent to stain leukocyte and endothelial cell lines. The leukocyte cell lines tested include TK1, HL60, HSB2, Raji, RAMOS, RPMI, JY, and THP-1. Among the leukocyte cell lines, only TK1 cells are positive when stained with LERK-2-Ig chimera, indicating that TK1 cells express a receptor for LERK-2, which is consistent with other results described herein (FIG. 4).

Figure 5:
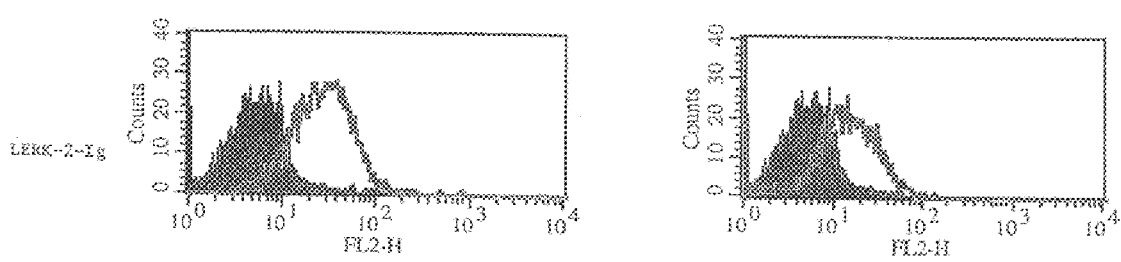
FIG. 5 shows the results of FACS analysis using a LERK-2 Ig chimera. These results indicate that HUVECS also express a receptor for LERK-2.

The expression of receptor for LERK-2 on HUVEC cells was also investigated in the presence or absence of TNF-α stimulation. The data showed that a receptor for LERK-2 is expressed on HUVEC cells, while TNF-α stimulation does not increase the expression of this receptor on HUVECs (FIG. 5).

Summary of LERK II Tissue Staining

The expression of LERK-2 in normal and inflamed human tissues by immunohistochemistry and flow cytometry (see Table). Human tissues (normal and inflamed) were obtained from the National Disease Research Institute, a service organization funded by the National Institutes of Health.

Immunohistochemical analysis for LERK-2 was performed on frozen tissue samples. Briefly, tissue was sectioned at a thickness of 4 mm, desiccated, and then fixed in 2% paraformaldehyde/0.5×PBS for 10 minutes at 4° C. After PBS washing, nonspecific antibody binding sites were blocked with 10% normal goat serum/5% human AB serum/PBS for 30 minutes at room temperature. Next the purified, LERK-2 murine antibody (4A1) was diluted to a concentration of 10 mg/ml in 0.3% Tritonx100/0.2% Tween 20/1% FCS/5% human AB serum/0.1% sodium azide and applied to tissue sections overnight at 4° C. An isotype-matched irrelevant monoclonal antibody (IgG1, MOPC21) was used as a negative control on step sections of tissues. Subsequently, biotinylated goat anti-mouse IgG and avidin-biotin-alkaline phosphatase complexes (Biogenex, San Ramon, Calif.) were added in sequence. Fast Red (Biogenex, San Ramon, Calif.), containing 2% levamisole to block endogenous alkaline phosphatase activity, was used as the chromogen and Mayers hematoxylin as the counterstain.

LERK-2 is widely expressed on vascular endothelium in all organs examined. The staining intensity is quite variable between tissues. In tissues, patchy staining of vascular smooth muscle is frequently observed. Sections of lymph node reveal staining on mononuclear cells (lymphocytes, monocyte/macrophages) within the subcapsular and medullary sinuses as well as the paracortex. In sections of inflamed colon, LERK-2 staining is sometimes more intense on endothelia of vessels adjacent to regions of inflammation.

While this invention has been particularly shown and described with references to preferred embodiments thereof, it will be understood by those skilled in the art that various changes in form and details may be made therein without departing from the spirit and scope of the invention as defined by the following claims.

What is claimed is:

1. A method of inhibiting LERK-2-mediated cell adhesion, comprising the step of contacting a cell expressing LERK-2 with an antibody produced by the hybridoma having American Type Culture Collection Accession No. HB-12412.

2. The method according to claim 1, wherein the cell expressing LERK-2 is a cell which bears LERK-2 in nature.

3. A method of inhibiting LERK-2-mediated cell adhesion, comprising the step of contacting a cell expressing LERK-2 with an antigen-binding fragment of an antibody produced by the hybridoma having American Type Culture Collection Accession No. HB-12412.

4. The method according to claim 3, wherein the cell expressing LERK-2 is a cell which bears LERK-2 in nature.

5. A method of inhibiting LERK-2-mediated cell adhesion, comprising the step of contacting a cell expressing LERK-2 with an antibody produced by the hybridoma having American Type Culture Collection Accession No. HB-12413.

6. The method according to claim 5, wherein the cell expressing LERK-2 is a cell which bears LERK-2 in nature.

7. A method of inhibiting LERK-2-mediated cell adhesion, comprising the step of contacting a cell expressing LERK-2 with an antigen-binding fragment of an antibody produced by the hybridoma having American Type Culture Collection Accession No. HB-12413.

8. The method according to claim 7, wherein the cell expressing LERK-2 is a cell which bears LERK-2 in nature.

* * * * *